United States Patent [19]

Saveliev et al.

[11] Patent Number: 4,943,297
[45] Date of Patent: Jul. 24, 1990

[54] DEVICE FOR PREPARATION OF INTRAVENOUS FILTER FOR IMPLANTATION

[76] Inventors: Viktor S. Saveliev, ulitsa Donskaya, 27, kv. 29; Evgeny G. Yablokov, Rogozhsky val, 6, kv. 45; Vladimir I. Prokubovsky, Khoroshevskoe shosse, 66, kv. 71, all of Moscow; Stepan M. Kolody, korpus 505, kv. 28, Moskovskaya oblast, Zelenograd; Sergei V. Saveliev, ulitsa Bolshaya Bronnaya, 9/I, kv. I6; Ary A. Smirnov, Leningradsky prospekt, 28, kv. I20, both of Moscow, all of U.S.S.R.

[21] Appl. No.: 294,468
[22] Filed: Jan. 6, 1989

[30] Foreign Application Priority Data
Jan. 2, 1988 [SU] U.S.S.R. .............................. 4351223

[51] Int. Cl.$^5$ ............................................. A61B 17/00
[52] U.S. Cl. ................................................... 606/200
[58] Field of Search ............... 128/303 R, 899, 348.1, 128/345; 606/200, 108

[56] References Cited

U.S. PATENT DOCUMENTS 3,540,431 11/1970 Mobin-Uddin ............... 128/325 X
4,793,359 12/1988 Sharrow ...................... 128/303.1 X

OTHER PUBLICATIONS

"Gunter Vena Cava Filter Set", Pamphlet by William Cook Europe.

Primary Examiner—Michael H. Thaler
Attorney, Agent, or Firm—Burgess, Ryan & Wayne

[57] ABSTRACT

The device comprises a guide element and an applicator which has a capsule adapted to accommodate an intravenous filter, a number of springs being located at the capsule base, said springs being so fashioned that their free ends are curved to define a pyriform body of revolution which encompasses the capsule. The applicator comprises also a conducting catheter, a sleeve installed on the catheter and so traversable as to get in contact with the springs, a stylet and a collet grip.

1 Claim, 2 Drawing Sheets

DEVICE FOR PREPARATION OF INTRAVENOUS FILTER FOR IMPLANTATION

FIELD OF THE INVENTION

The invention relates generally to medical equipment and apparatus and more specifically to a device for preparation of an intravenous filter for implantation.

The invention is applicable for treatment and/or prevention of thromboembolism of the pulmonary artery by way of transcutaneous implantation of an intravenous filter by the subclavian or femoral vein approach.

BACKGROUND OF THE INVENTION

Known in the art of a device for preparation of an intravenous filter for implantation, which comprises a conducting catheter, a catheter introduction system, a filter fixing hook and a filter holding hook.

The filter holding hook is passed through the catheter, caught by a corresponding hook on the filter holder and the filter is pulled into the catheter, whereupon the filter is ready for implantation (cf. a prospectus of the firm Cook entitled "Gunter vena cava filter set" No. 600.4.85).

One more state-of-the art device for preparation of an intravenous filter for implantation is known to comprise a guide element having a cylindrical portion and a conical portion, as well as an applicator provided with a capsule for accommodating an intravenous filter, a conducting catheter connected to said capsule, a stylet and a collet grip. The stylet is accommodated inside the catheter and capsule and has a screw for the filter to be retained (U.S. Pat. No. 3,540,431).

To prepare the filter for implantation the stylet is passed through the capsule and catheter with its plain unthreaded end forward, whereupon the filter is screwed onto the stylet thread and is introduced, through the conical portion of the guide element, into its cylindrical portion, with the result that the filter gets folded up. Then the hole of the capsule is brought in register with that of the cylindrical portion, and the filter is made to move into the capsule, by virtue of retrograde traction of the stylet, and the capsule is withdrawn, together with the filter, from the guide element. The assembly procedure terminates in locking the stylet in position by means of the collet grip.

Implantation of an intravenous filter enclosed in any heretofore-known device is possible only through the right internal jugular vein, that is, by the so-called "retrograde" technique. Besides, to fold up the filter requires much effort to be applied, while its introducing into the capsule is fraught with damages to the filter construction, which are likely to be the cause of repeated thromboembolism of the pulmonary artery.

It is not infrequently that the intravenous filter is implanted, with the aid of the known device, in an angular position with respect to the longitudinal axis of the vena cava inferior, and the angle of inclination owes its origin from the fact that the applicator capsule has not been centred with respect to the vena cava inferior. Hence, an inclined position of the filter will result in its wrong unstable arrangement, which might be the cause of repeated thromboembolism of the pulmonary artery or proximal filter migration.

SUMMARY OF THE INVENTION

It is an object of the present invention to provide a device for preparation of an intravenous filter for implantation, which would make it possible to centre the capsule with the intravenous filter lengthwise the vena cava inferior.

It is another object of the present invention to reduce the number of repeated implantations of the filters due to wrong and unstable filter position in the course of the initial implantation.

The foregoing and further objects of the invention are accomplished due to the fact that a device for preparation of an intravenous filter for implantation, according to the invention, comprises a guide element, which has a cylindrical portion and a conical portion, as well as an applicator having a capsule adapted for the intravenous filter to be accommodated therein, a number of springs being located at the base of said capsule, said springs being so fashioned that their free ends are curved to define a pyriform body of revolution encompassing the capsule, a conducting catheter connected to the capsule, a sleeve installed on the catheter traversably lengthwise the latter and adapted to interact with the springs, a stylet accommodated inside the conducting catheter and capsule and having a thread for holding the intravenous filter, a collet grip adapted to interact with the stylet.

This enables the capsule with the intravenous filter to be positioned strictly symmetrically with respect to the vena cava inferior and hence to symmetrically fix the filter in said vein.

BRIEF DESCRIPTION OF THE DRAWINGS

Further objects and advantages of the invention will become apparent from a consideration of a specific exemplary embodiment thereof with reference to the accompanying drawings, wherein.

DETAILED DESCRIPTION OF THE INVENTION

Figure 1:
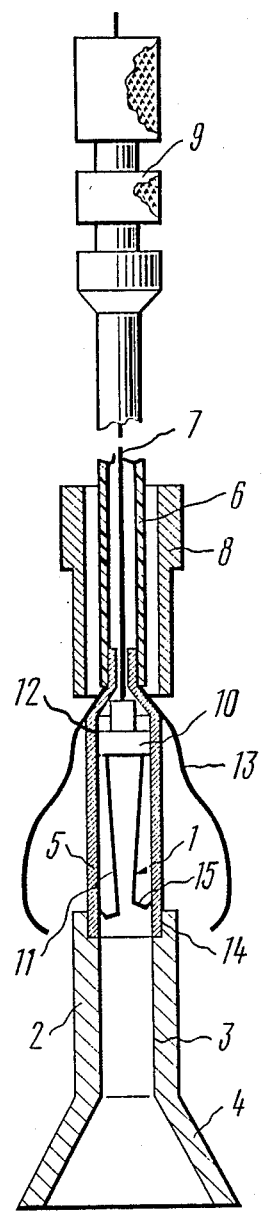
FIG. 1 is a general view of a device for preparation of an intravenous filter for implantation, according to the invention.

The device for preparation of an intravenous filter 1 (FIG. 1) for implantation comprises a guide element 2 and an applicator. The element 2 has a cylindrical portion 3 and a conical portion 4. The applicator has a capsule 5, a conducting catheter 6, a stylet 7, a sleeve 8 and a collet grip 9. The capsule 5 is adapted to interact with the cylindrical portion 3 of the guide element 2. The capsule 5 accommodates the filter 1, which has a holder 10, wherein a number of elastic rods 11 are made fast.

A plurality of springs 13 are situated at a base 12 of the capsule 5 as shown in FIG. 1. The free end of each spring 13 is so bent that the free ends of all the springs 13 define a pyriform body of revolution. The springs 13 thus encompass the capsule 5.

Connected to the capsule 5 is the catheter 6, which carries the sleeve 8 mounted transversely lengthwise the catheter 6. The stylet 7 is accommodated inside the capsule 5 and the catheter 6, said stylet being interlinked with the holder 10 of the filter 1 and holds the filter 1 through a threaded joint with the holder 10. The other end of the stylet 7 is fixed in the collet grip 9.

The device for preparation of the intravenous filter for implantation operates as follows.

The applicator capsule 5 is fitted into a seat 14 of the cylindrical portion 3 of the guide element 2. The threaded end of the stylet 7 is withdrawn from the conical portion 4 of the guide element 2 and screwed into the holder 10 of the filter 1. The other stylet end passing through the catheter 6, is fixed in the collet grip 9. Then the filter 1 is passed, by the stylet 7, through the guide element 2 and introduced into the capsule 5, with the result that the elastic rods 11 with catches 15 are compressed and arranged inside the capsule 5.

Figure 2:
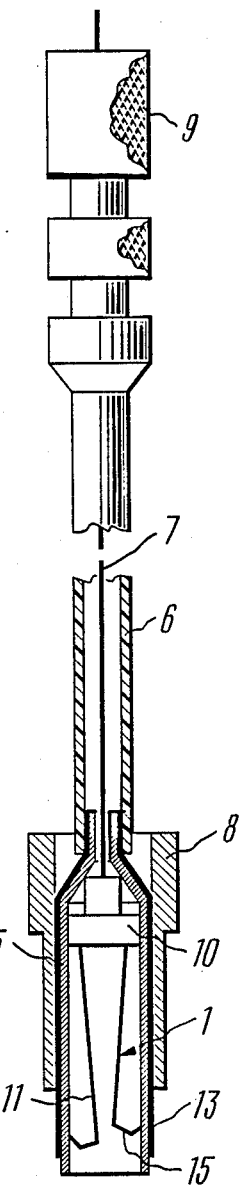
FIG. 2 is a view of the device of FIG. 1 with the springs brought together.

Next the capsule 5 is removed from the positioning seat 14 of the guide element 2 and the sleeve 8 is moved towards the springs 13 and, while running against their ends connected to the holder 10, brings the free ends of the springs 13 together until they come in an intimate contact with the outside surface of the applicator capsule 5 as shown in FIG. 2. Thus, the device is ready for implantation of the filter 1.

The "retrograde" implantation technique is carried out as follows.

After a Seldinger's puncture a cannula (omitted in the Drawing) is introduced, under topical anesthesia, into the subclavian vein or into the internal jugular vein, whereupon the cannula is passed into the vena cava superior, the right cardiac atrium, and the vena cava inferior downstream of the openings of the renal veins to the level of the second lumbar vertebra; next the applicator capsule 5 is guided, under Ro-scopy and TV monitoring, through the vena cava inferior to the level of the lower edge of the second lumbar vertebra. At the instant when the applicator capsule 5 emerges from the cannula the springs 13 center the capsule in the vena cava inferior due to the fact that the springs establish a pyriform body of revolution, and the maximum-diameter portion of said body of revolution adheres tightly to the wall of the vena cava. The true pyriform shape of said body of revolution is not distorted due to elasticity of the springs which form said body. Thus, the axis of the capsule 5 and hence that of the filter 1 gets centred lengthwise the axis of the vena cava. Then the filter 1 is brought out of the capsule 5 with the aid of the stylet 7, which is followed by traction of the entire applicator upwards in order to fix it in the vena cava inferior. Thereupon the collet grip 9 is given several turns counterclockwise to disengage the applicator from the thus-implanted filter 1 and the applicator is removed from the vena cava along with the cannula. As a result, the holder 10 of the filter 1 proves to be positioned more proximally than the fixing L-shaped catches 15, while the curved elastic rods 11 symmetrically converging at the centre and secured in the holder 10, form an embolus localization zone. The springs 13 retain the capsule 5 with the filter 1, in the course of surgery, in a symmetrical position inside the vena cava inferior. Finally, an aseptic patch is applied to the puncture wound.

The antegrade intravenous filter implantation technique by the femoral vein approach is carried out as follows.

After a Seldinger's puncture a cannula (omitted in the Drawing) is introduced, under topical anesthesia, into the femoral vein, whereupon the cannula is passed through the iliac veins into the vena cava inferior as far as the level of the second lumbar vertebra; next the applicator capsule 5 is guided, under Ro-scopy and TV monitoring, through the vena cava inferior to the level of the upper edge of the body of the second lumbar vertebra. At the instant when the applicator capsule 5 emerges from the cannula the springs 13 urge the capsule to get centred in the vena cava inferior below the openings of the renal veins. Further on the filter 1 is brought out of the capsule 5 with the aid of the stylet 7, which is followed by traction of the entire applicator upwards in order to fix it in the vena cava inferior. Next the collet grip 9 is given several revolutions counterclockwise to disengage the applicator from the thus-implanted filter 1 and the applicator is removed from the vena cava along with the cannula. As a result, the holder 10 of the filter 1 is arranged in the direction of blood flow through the vena cava inferior. Finally, an aseptic patch is applied to the puncture wound.

The herein-proposed device has been trialled on a total of 27 patients with thromboembolism of the pulmonary artery by way of transcutaneous implantation of intravenous filters, of which in 18 cases the implantation has been performed by the retrograde technique and in 9 cases, by the antegrade technique.

No repeated thromboembolism has been noticed in any one of the patients operated upon.

Practical application of the invention enables one to perform an efficacious roentgeno-endovascular prevention of massive thromboembolism of the pulmonary artery by the low-traumatic puncture retrograde and antegrade techniques in extremely grave patients with floating thromboses in the vascular bed of vena cava inferior.

What is claimed is:

1. A device for preparation of an intravenous filter for implantation, comprising:
   a guide element having a cylindrical and a conical portion; an applicator, comprising:
   a capsule which is detachably connected with said cylindrical portion of the guide element, said capsule carrying an intravenous filter and having a base;
   a plurality of springs located at said base; each of said springs having one end contacting said base and the other end free; each of said springs curved in such a manner that said free end of said spring, together with the free ends of all of said springs define a pyriform body of revolution, which encompasses said capsule;
   a conducting catheter connected to said capsule;
   a sleeve installed on said catheter and traversable lengthwise said catheter during preparation for surgery in order to interact with said springs, thus urging said free ends of said springs to be brought together until they are in contact with said capsule;
   a stylet accommodated inside said catheter and said capsule and having a thread for holding said intravenous filter; and
   a collet grip adapted to interact with said stylet.

* * * * *